United States Patent
Galanis et al.

(10) Patent No.: US 12,115,041 B2
(45) Date of Patent: Oct. 15, 2024

(54) COMPRESSION GARMENT

(71) Applicants: Charles J. Galanis, Los Angeles, CA (US); Johnathan Caruso, Brooklyn, NY (US); Melinda Kelly, Los Angeles, CA (US); Corrine Conley, Los Angeles, CA (US)

(72) Inventors: Charles J. Galanis, Los Angeles, CA (US); Johnathan Caruso, Brooklyn, NY (US); Melinda Kelly, Los Angeles, CA (US); Corrine Conley, Los Angeles, CA (US)

(73) Assignee: Muse No 10 Inc., Los Angeles, CA (US)

( * ) Notice: Subject to any disclaimer, the term of this patent is extended or adjusted under 35 U.S.C. 154(b) by 626 days.

(21) Appl. No.: 17/381,912

(22) Filed: Jul. 21, 2021

(65) Prior Publication Data

US 2023/0022339 A1 Jan. 26, 2023

(51) Int. Cl.
*A61F 13/14* (2006.01)
*A41C 1/06* (2006.01)

(52) U.S. Cl.
CPC .............. *A61F 13/145* (2013.01); *A41C 1/06* (2013.01)

(58) Field of Classification Search
CPC ................................. A41C 1/06; A61F 13/145
See application file for complete search history.

(56) References Cited

U.S. PATENT DOCUMENTS

| | | | |
|---|---|---|---|
| 2,963,022 A * | 12/1960 | Spetalnik | A41C 1/06 450/15 |
| 3,110,313 A * | 11/1963 | Plehn | A41C 1/06 2/DIG. 9 |
| 3,890,979 A * | 6/1975 | Fierst | A41C 1/06 450/131 |
| 4,983,140 A * | 1/1991 | Gimble | A41C 1/06 450/35 |
| 5,429,593 A | 7/1995 | Matory | |
| 5,537,690 A | 7/1996 | Johnson | |
| D410,688 S | 6/1999 | Robinson | |
| D503,509 S | 4/2005 | Bell et al. | |
| 8,506,509 B1 | 8/2013 | Ariza | |
| 8,574,025 B2 | 11/2013 | Kent | |
| 8,695,115 B2 | 4/2014 | Leyva | |
| 9,320,306 B2 | 4/2016 | Freddi et al. | |
| 9,743,692 B2 | 8/2017 | Palese | |

(Continued)

FOREIGN PATENT DOCUMENTS

| | | |
|---|---|---|
| AU | 323615 S | 1/2009 |
| CN | 103462247 B | 4/2015 |

(Continued)

*Primary Examiner* — Gloria M Hale
(74) *Attorney, Agent, or Firm* — Fitzpatrick PC

(57) ABSTRACT

A compression garment for a maximizing pressure on a soft-tissue area of a user, the garment is provided. The compression garment has a breast section, a first horizontal anchor positioned connected to the bottom of the breast section, an umbilical and hypogastric section connected to the latissimus dorsi section, a second horizontal anchor positioned and connected to the top of the umbilical and hypogastric, and a third anchor positioned and connected to the bottom of the lumbar and iliac section, wherein the fourth horizontal anchor is configured support the lumbar and iliac section.

15 Claims, 7 Drawing Sheets

(56) References Cited

U.S. PATENT DOCUMENTS

| | | | |
|---|---|---|---|
| 9,936,739 B2 | 4/2018 | Smith | |
| 2008/0092265 A1 | 4/2008 | Gage et al. | |
| 2009/0138064 A1 | 5/2009 | Horn | |
| 2012/0012104 A1 | 1/2012 | Yacov | |
| 2013/0095730 A1 | 4/2013 | Jensen | |
| 2014/0031775 A1 | 1/2014 | Criss | |
| 2014/0209102 A1 | 7/2014 | Smith | |
| 2015/0245670 A1* | 9/2015 | Angelino | A41C 1/003 |
| | | | 450/143 |
| 2016/0015088 A1* | 1/2016 | Hendrickson | A41C 1/06 |
| | | | 450/95 |
| 2017/0309204 A1 | 10/2017 | Feins et al. | |
| 2018/0360132 A1* | 12/2018 | Melarti | A41C 1/12 |
| 2019/0388280 A1 | 12/2019 | Stephens et al. | |
| 2023/0022339 A1* | 1/2023 | Galanis | A41C 1/06 |

FOREIGN PATENT DOCUMENTS

| | | |
|---|---|---|
| CN | 103987287 B | 1/2016 |
| CN | 106031677 A | 12/2016 |
| CN | 205866006 U | 1/2017 |
| CN | 210728002 U | 6/2020 |
| EP | 3287107 B1 | 7/2020 |
| GB | 2482760 A | 2/2012 |
| JP | 2021001432 A | 1/2021 |
| WO | 2019177993 A1 | 9/2019 |
| WO | 2019218059 A1 | 11/2019 |

* cited by examiner

COMPRESSION GARMENT

TECHNICAL FIELD

The present disclosure generally relates to compression garments to be worn by individuals or user. More specifically, the present disclosure relates to post-surgical and body contouring garments worn by patients that have undergone certain treatments.

BACKGROUND

Compression garments are pieces of clothing that fit tightly around the skin. In a medical context, compression garments provide support for people who have undergone certain surgeries or treatments. These garments come in varying degrees of compression—for example, higher degree compression sleeves, such as sleeves that provide compression of 20-30 mmHg or higher, typically require a doctor's prescription.

Shaping garments on the other hand are undergarments used for body contouring and have been vastly popularized in the last decade, even though the original shaping garment—the corset—has been used for many hundreds of years.

The application of sustained graduated compression is a key element in the treatment of all types of surgical sites. Compression garments used for post-surgical care to assist with the healing process. Garment type and usage vary depending upon the type of operation or surgery the patient has undergone, but can be worn for up to a year. Further, the type garment the patient requires may vary over time for the same user based on the same surgery.

As one of a myriad of examples, compression garments are used after liposuction procedures to help the skin at a surgical site reattach to the lower dermal layer. Physicians have used different types of compression wear for many years to help reshape patient body contours after sub-dermal intervention. Such garments are necessary because a human body naturally heals itself by swelling. Unfortunately, swelling can cause the improper reattachment of the skin to its new contours. Swelling can also break or dislocate wound healing tapes, sutures, staples, or other devices.

The degree of compressive pressure required to optimize wound healing is multivariant based on the nature and degree of severity of the surgery and the persons natural tendency or ability heal. The effectiveness of compression garments depends upon pressure provided and thus is determined by several factors including the physical and elastomeric properties of the fabric, the size and shape of the site, and points of tension garment post application.

Like stocking or tubular bandages, the relationship between extension (a function of site diameter) and fabric tension is 'pre-programmed' into the product during the manufacturing process, the tension developed garments is determined entirely by manufacturer and the person wearing it. Tension establishing applied pressures at the wound/surgery site often determines of the effectiveness of the treatment. If the pressure achieved is too low, the compression may be ineffective to prevent swelling and stretching. But if the pressure is excessively high there is a real possibility the resulting compression can damage tissue and cause necrosis over vulnerable areas.

Historically, attempts have been made to form compression garments that are useful depending upon the time it needs to worn. Many post-surgical are used immediately following surgery, sometimes referred to as Step 1 or Stage 1, which may be work 0-4 weeks after surgery, Step 2 or Stage 2 which may be worn 4-12 weeks after surgery, and step 3 or stage 3 garments work 12 weeks plus. A myriad of studies show medical-grade compression may help reduce swelling, help reduce bruising, improve the ability to sleep in comfort, provide ease of movement and further assist post-surgical aesthetics.

An example, U.S. Pat. No. 8,506,509B1 to Hoyas describes compression garment for treating post-operative patients involved in body contouring surgery and including a base structured for removable disposition in an operative position about the torso and other portions of the patient's body. The compression garment is dimensioned, configured and structured to apply appropriate compression to the surgically affected portions of the patient in order to reduce pain, diminish swelling and avoid fluid accumulation, while not impairing the venous and lymphatic circulation of the affected body portion. The base has one or a first and second cover member overlying its internal and external faces and a closure assembly serves to maintain the garment in a variable closed orientation such that appropriate compressive force may be applied to the affected body areas.

However, these and other types of surgical compression garments do not properly apply compressive forces to the affected area based the multiple variables described above, and further, are bulky and thus are not optimal to be worn under clothing.

Further, the known compression and devices have drawbacks including conforming to proper mimicking of a myriad of potential procedures and lack support in the proper areas of interest based on the procured the patient has undergone. Further, the prior art devices are single-purpose devices (e.g., stage 1 vs. stage 2 post-operative care) and are inadequate to be worn as an undergarment while also applying proper pressure.

Considering the above-mentioned drawbacks, there is a need for a new compression device that obviates the drawbacks of the prior compression garments.

SUMMARY

The present disclosure generally discloses a compression garment. More specifically, the present disclosure relates to post-surgical compression garments worn by patients that have undergone certain treatments (e.g., medical, or medicinal) and may be worn comfortably as an undergarment post-surgery. Further, the garment can be worn as a stand-alone garment. In this way, while it has surgical-grade compression, it has the look and feel of sportswear.

In embodiments, the garment is constructed to mimic or simulate certain surgical techniques such as, but not limited, to liposuction, abdominoplasty, butt augmentation (BBL) and the like.

In embodiments, both laterally and posteriorly, the garment maximizes compression at the waistline soft tissue using highly compressive, double-layer fabric anchored at bordering boney anchor points or landmarks, namely, the rib cage and iliac crest (hip bone) and other bony areas depending upon a type of procedure or desired effect. In the center abdomen, compression continues over the soft tissue using the bordering boney anchor points of the central rib cage, pubic bones and trochanter bones.

In embodiments, additional support may be provided along the user's semilunar lines at the lateral border of the rectus muscle and is configured to further enhance both compression and the overall aesthetic contour mimicking surgical high-definition contouring principles.

In embodiments, a lesser compressive single-layer fabric is attached to certain anchoring portions used to compress and smooth soft tissue which lies directly over the bone such as the skin under the breast overlying the lower rib cage. Whether or not the fabric is single payer or double layer, the boney landmarks serve as anchor points to support anatomical compression for optimal body contouring, in other words, compression occurs at the soft tissue and anchor point are at boney landmarks (rib cage, iliac crests, pubic symphysis).

In an embodiment, a compression garment for a maximizing pressure on a soft-tissue area of a user is provided. The garment comprises a breast section positioned proximate the pectoralis major and breast of the user, wherein the breast section is constructed of single layer fabric cut on grain. A latissimus dorsi and serratus anterior section connected to the breast section is provided, wherein the latissimus dorsi and serratus anterior section is constructed of the single layer fabric cut on grain. A first horizontal anchor positioned connected to the bottom of the breast section is provided, wherein the first horizontal anchor is configured to support the latissimus dorsi and serratus anterior portion. An umbilical and hypogastric section connected to the latissimus dorsi section is provided, wherein the umbilical and hypogastric section is constructed of double-layer fabric cut on cross grain and configured to smooth soft tissue which lies over the umbilical and hypogastric section of the user. A second horizontal anchor positioned and connected to the top of the umbilical and hypogastric is provided, wherein the second horizontal anchor is configured support the umbilical and hypogastric section. A lumbar and iliac section connected to the umbilical and hypogastric section is provided, wherein the lumbar and iliac section is constructed of the single layer fabric cut on grain, and a third anchor positioned and connected to the bottom of the lumbar and iliac section, and wherein the forth horizontal anchor is configured support the lumbar and iliac section.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF DRAWINGS

The foregoing summary, as well as the following detailed description of the disclosure, is better understood when read in conjunction with the appended drawings. For the purpose of illustrating the disclosure, exemplary constructions of the disclosure are shown in the drawings. However, the disclosure is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF EMBODIMENTS

Figure 1:
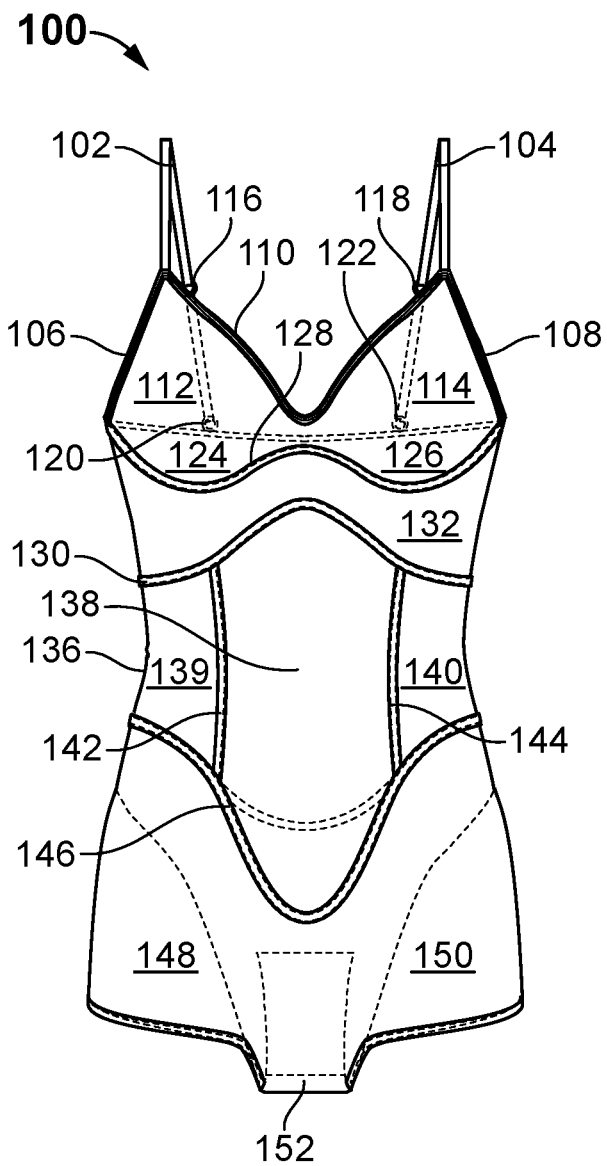
FIG. 1 shows a front view of a compression garment according to an embodiment.

The present disclosure is best understood by reference to the detailed figures and description set forth herein.

It is expected that the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes that come within the meaning and range of equivalency of the claims are to be embraced within their scope.

Embodiments of the system are discussed below with reference to the examples. However, those skilled in the art will readily appreciate that the detailed description given herein with respect to these examples is for explanatory purposes as the system extends beyond these limited embodiments. For example, it should be appreciated that those skilled in the art will, in light of the teachings of the present system, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the system that are too numerous to be listed but that all fit within the scope of the system. Also, singular words should be read as plural and vice versa and masculine as feminine and vice versa, where appropriate, and alternative embodiments do not necessarily imply that the two are mutually exclusive.

It is to be further understood that the present system is not limited to the particular methodology, compounds, materials, manufacturing techniques, uses, and applications, described herein, as these may vary. It is also to be understood that the terminology used herein is used for the purpose of describing particular embodiments only and is not intended to limit the scope of the present system. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this system belongs. Preferred methods, techniques, devices, and materials are described, although any methods, techniques, devices, or materials similar or equivalent to those described herein may be used in the practice or testing of the present system.

As used herein "boney anchor points" refer to regions of the garment in which the anchors of the garment are connected to a portion of the garment that overlays an area that is boney and thus provides support for the compressive materials of the garment. While in some embodiments seems may act as anchors, other times double-fabric layers such as those shown at the upper region of lumbar and iliac section 148 and 150 act as anchors because they settle on boney regions (e.g, hip or pelvic bones). These are considered upper regions of the sections.

As used herein, "grain" refers to the orientation of the weft and warp threads. The three named grains are straight grain, cross grain, and the bias grain. In sewing, a pattern piece can be cut from fabric in any orientation, and the chosen grain or orientation affects the way the fabric hangs and stretches and thus the fit of a garment.

As used herein, "cut on grain" means to be cut on a particular grain when the main seams of the finished piece are aligned with that grain.

As used herein, "cut cross grain" means cut so the cross grain runs perpendicular to the selvedge and parallel to the weft threads.

As used herein, when referring to a "lesser compressive" fabric, it is meant the fabric is relatively less compressive or has less tensile strength or more stretch than the double layer fabric described herein.

Referring to FIG. 1, a front view of a compression garment 100 is shown. The compression garment 100 may be worn by a patient during post-operative care, for example, after a medical procedure such as a tummy-tuck of liposuction and further, to be worn comfortably as an undergarment post-surgery or to be worn as a stand-alone garment. The compression garment 100 maximizes pressure on a soft-tissue area of a user and comprises a plurality of different sections that are defined by bordering anchoring portions and anchoring lines that are shaped for certain medical purposes. The anchoring lines may act as anchor buttresses proximate bony landmarks that serve as anchor points to support and provide compression for optimal body contouring. In this way, the garment provides for different sections or partitions separated by anchoring lines (in some embodiments, seams) such that the separate sections provide for smoothing of the soft tissue thereunder.

Right and left breast section 112 and 114, a latissimus dorsi and serratus anterior section 132, an umbilical and hypogastric section 138, and a lumbar and iliac section 148, 150, each of which have different compression characteristics.

As shown in FIG. 1, the compression garment 100 comprises right shoulder strap 102 and left shoulder straps 104. The shoulder straps 102 and 104 are configured to retain the garment in a vertical position and are further configured to provide a lifting support to a breast portion of the user. The shoulder strap, in some embodiments, may be constructed or manufacturer of a of double layer suede for both conform and to prevent chafing. In embodiments, the shoulder straps comprises a right adjustable member 116 and a left adjustable member 118 attached to the at least one shoulder strap. The adjustment members, in embodiments, may be O-rings having a rubberized finish and configured to allow a user to adjust the vertical fit of the garment.

Referring still to FIG. 1, a right breast section 112 and a left breast section 114 are provided and are positioned proximate the pectoralis major and deltoid of the user. The right and left breast sections 112 and 114 are connected to the straps 102 and 104 via top section 110 of bralette, which comprises right portion 106 and left portion 108.

The breast sections 112 and 114 may be constructed of single layer fabric cut on grain and lined with high or heavy power mesh spandex to provide appropriate support and breathability. In operation, the breast sections 112 and 114 operate together with straps 102 and 104 to ensure the breast region is appropriately supported and yet compressed.

Referring still to FIG. 1, a bralette comprises a top section 110 and right portion 106 and left portion 108 configured to provide attachment points for the straps 102 and 104. The top section 110 and the first horizontal anchor 128 act to define the breast portions 112 and 114 and under-breast portions 124 and 126. In operation, the top section 110 is an approximate rounded V-shape, and rests on the clavicle region of the user. In this way, it is connected to top of the breast section proximate a clavicle region of the user, is configured to support the breast section.

Still with reference to FIG. 1, a first horizontal anchor 128 is provided and is positioned at the bottom of the breast sections 112 and 114. The first horizontal anchor 128 is configured to support and define the latissimus dorsi and serratus anterior portion 132, while also providing an anchor point at boney portion of the user in that area. In operation, the first horizontal anchor wherein the second horizonal anchor has an upward sinusoidal curved profile in relation to the user's lower breast 124 and 126. The first anchor 128 may be manufactured from a material that has a high tensile strength or may be a seam that protects the stitching thereunder.

The latissimus dorsi and serratus anterior section 132 that is defined by the first horizontal anchor 128 and second horizontal anchor 130 may be constructed of the single layer fabric cut on grain like the breast section and lined with high or heavy power mesh spandex to provide appropriate support and breathability. In operation, the latissimus dorsi and serratus anterior section 132 operate together with first anchor 128 and second anchor 130 to ensure the user's skin over the latissimus dorsi and serratus anterior section 132 is supported, smoothed and compressed.

Below the latissimus dorsi and serratus anterior section 132, an umbilical and hypogastric section 138 is connected thereto. The umbilical and hypogastric section 138 is defined by the second anchor 130 and third horizontal anchor 146 may be constructed of a of double-layer fabric cut on cross grain and configured to smooth soft tissue which lies over the umbilical and hypogastric section or regions of the user. The latissimus dorsi and serratus anterior section 132 also comprises a heavy power mesh, again, cut cross grain. In this way, an umbilical and hypogastric section 138 has a stronger or higher tensile strength than the other layers. The umbilical and hypogastric section 138 is also sectioned vertically by a right vertical seam 142 and left vertical seam 144, further discussed below with relation to FIG. 3. In embodiments, a first layer of the double layer fabric is a polyester and spandex blend, and the second layer is applied binding with luster soft finish.

The second horizontal anchor 130 is provided and is positioned at the top of the umbilical and hypogastric section 138. Like the first horizontal anchor 128, the second horizontal anchor 130 is configured to support and define the umbilical and hypogastric section 138, while also providing an anchor point approximately seven (7) millimeters (mm)

below a rib line of the user. In operation, the second horizontal anchor 130 has an upward bell curved profile in relation to the user's lower breast 124 and 126. Like the first anchor 128, second anchor may be 130 may be manufactured from a material that has a high tensile strength or may be a seam that protects the stitching thereunder.

Below the umbilical and hypogastric section 138, lumbar and iliac section 148 and 150 is defined by the second anchor 130 and third anchor 146. The lumbar and iliac section 148 and 150 may be constructed of a of single layer fabric cut on grain and lined with high powered mesh and configured to smooth the soft tissue thereunder, but also act as an additional anchor (fourth anchor) because they define a boney region of the user and are made of a fabric that is durable to act as an anchor at the upper regions of sections 148 and 150.

The third anchor 146 is provided and is positioned at the bottom of the umbilical and hypogastric section 138 and top of the lumbar and iliac section 148 and 150. Like the second horizontal anchor 146, the third horizontal anchor 146 is configured to support and define the umbilical and hypogastric section 138 and the lumbar and iliac section 148 and 150. In operation, the third horizontal anchor 146 has a downward bell curved profile in relation to the user's lower breast 124 and 126. Like the first anchor 128, and second anchor 130, third anchor 146 may be manufactured from a material that has a high tensile strength or may be a seam that protects the stitching thereunder. The third anchor 146 is positioned approximately seven (7) millimeters (mm) above a hip line of a user, and each anchor portion is configured to compress, smooth, provide separation, structure, support, and shape for smoothing of a user's skin.

Still with reference to FIG. 1, a right vertical seam 142 is provided and connected to the second anchor 130 and third anchors 146. The first (or right) vertical seam defines a right lumbar region of the user 134 and the second (or left) vertical seam 144 connected to the second anchor 130 and third anchors 146, wherein the first vertical seam defines a right lumbar region of the user. The right vertical seam 142 and left vertical seam 144 are configured to provide longitudinal support to the garment and keep the garment in place. The vertical seams are configured to flatten the stomach and a pull the garment in both vertical and horizontal directions to stabilize the garment and the stomach region, and further, provide additional structure to the garment itself.

A panty liner 152 is provided in the lumbar and iliac section 148. The panty liner 152 is cut on grain and attached to the third anchor and further comprises a snap or self-fabric hook (e.g., Velcro®). The panty liner is configured to hold the garment in place when the snap or self-fabric connected.

Figure 2:
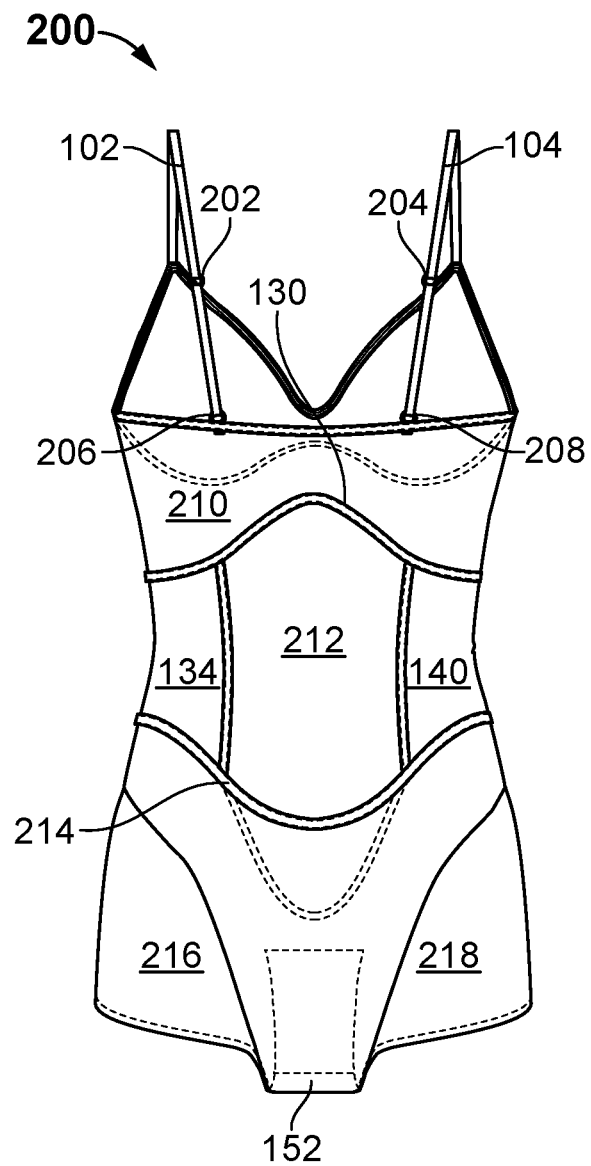
FIG. 2 shows a back view of a compression garment according to an embodiment.

Referring now to FIG. 2, a back portion of the compression garment is shown generally at 200. As can be seen, the back of the straps 202 and 204 and back connectors 206 and 208 are shown. These connect the upper back portion 210 to the garment. Upper back portion 210 is positioned above second anchor 130. Under second anchor at 130 is a mid-back portion to 212 which is defined by second anchor 130 and the back of third anchor 146 which is shown at 214 due to its slightly different curvature on the backside. The back of iliac sections 148 and 150 are shown at reference numeral 216 and 218. The back 214 of third anchor is shaped as a shallower upside-down bell curve due to the user's buttocks region. The back is configured to smooth out excess fat sections that section 140 didn't capture. Further, back anchor point anchors on the tailbone of the user.

Figure 3:
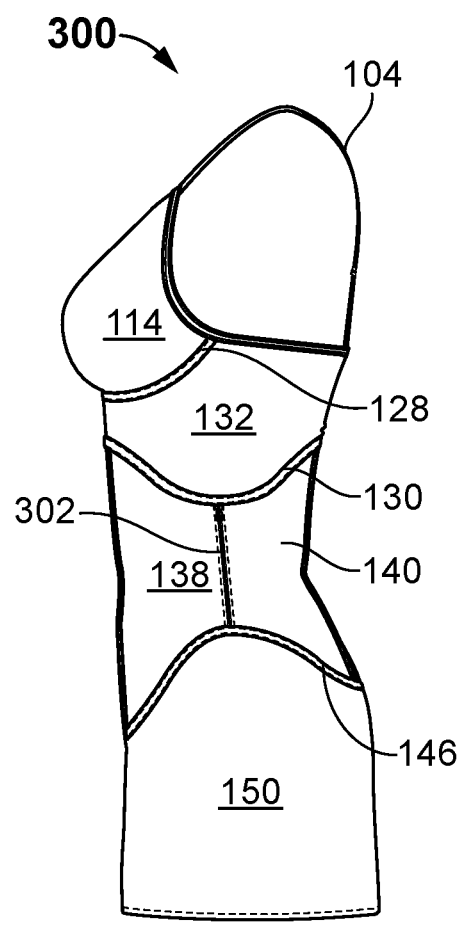
FIG. 3 shows a side view of a compression garment according to an embodiment.

Referring now to FIG. 3, a side view of the compression garment is shown generally at 300. For purposes of orientation, the strap 104, breast section 114, latissimus dorsi and serratus anterior section 132, umbilical and hypogastric section 138, and lumbar and iliac section 148, 150 are shown. In this embodiment, fastener 302 is provided to allow the user to more easily put on and take off the garment. The fastener may be located on front, back, right or left portions, and is discussed in greater detail with relation to FIG. 6.

Figure 4:
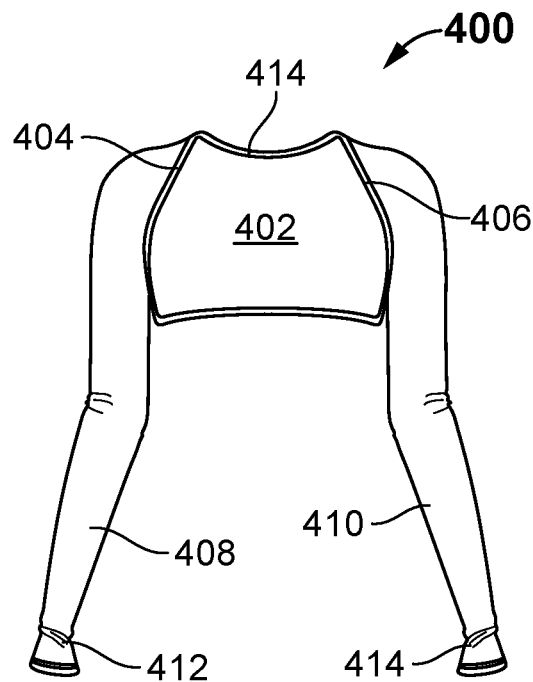
FIG. 4 shows a front view of a sleeved compression garment according to one an embodiment.
Figure 5:
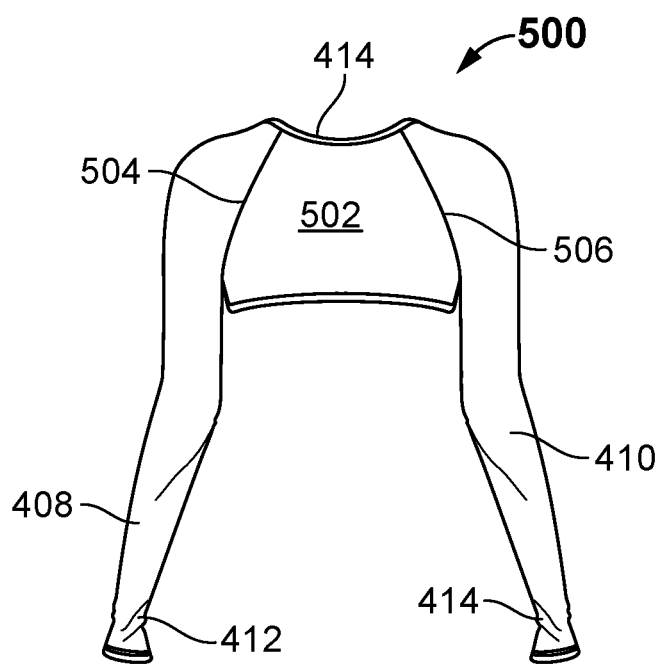
FIG. 5 shows a back view of the sleeved compression garment according to an embodiment.

Referring now to FIG. 4 and FIG. 5, a compression shrug that may be worn together or separate with the garment 100 is shown generally at 400. The shrug 400 comprises a chest section 402, shrug anchor 404, left shrug anchor 406 and a collar for 414. Right arm 408 and left arm 410 comprise restrictions 412 and 414 on each arm respectively. The back section of the shrug is shown at 500 and has back section 502 and shows the back of shrug anchors 504 and 506.

Figure 6:
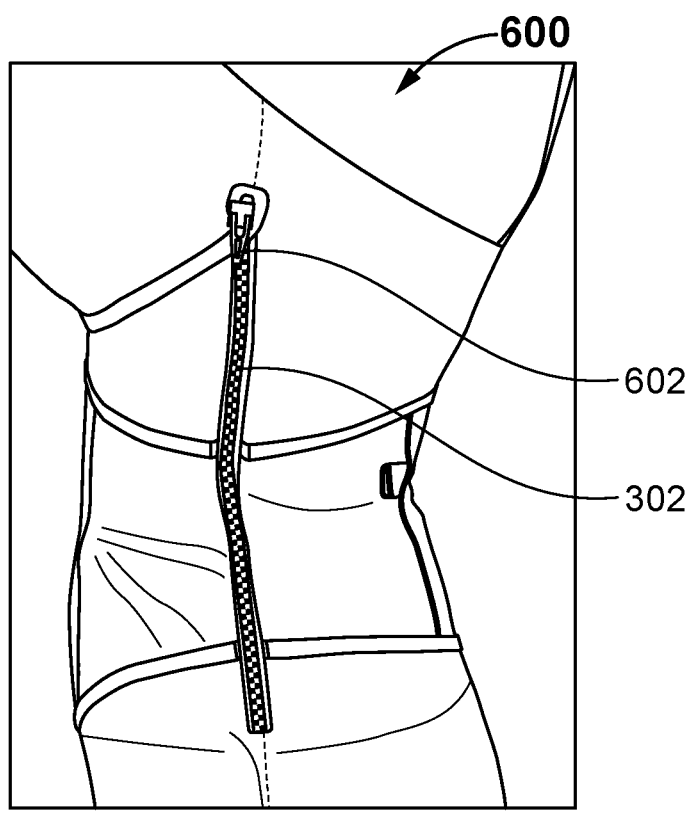
FIG. 6 shows a side view of a compression garment with a fastener according to an embodiment.

Referring now to FIG. 6, a side view showing the fastener is show at 600. The fastener 602 positioned on a left or right portion of the user extending from the iliac region to the breast region of the user but may be a front or back fastener as well. The fastener 602 is a zipper configured provides ease of garment entry, exit, and closure, and produce a high level of compression when in a closed position. The zippers may be a reverse zipper with an internal guard and an exterior reinforcement portion.

Figure 7:
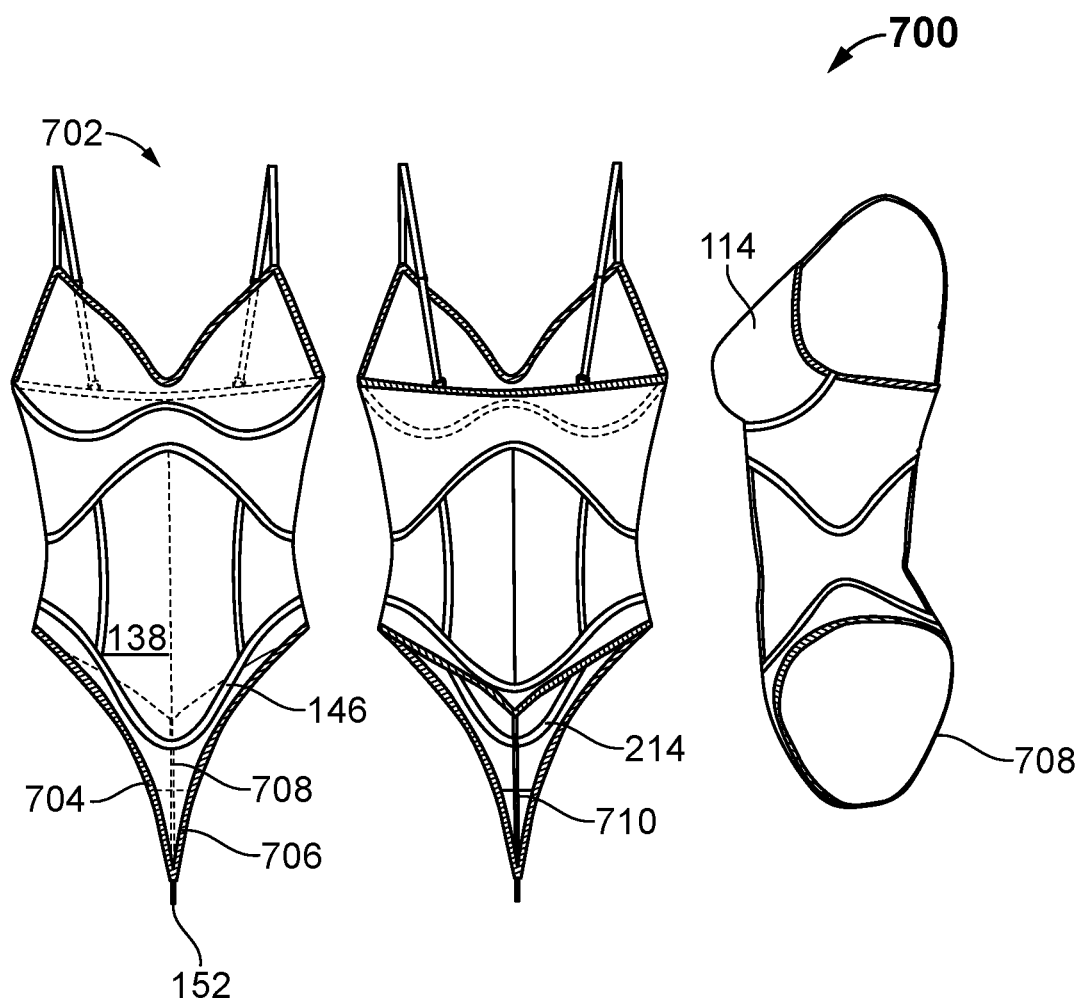
FIG. 7 shows a front, back and side view of a thong according to an embodiment.

Referring now to FIG. 7, a compression garment 700 is shown, but in this embodiment, there are no leg portions, but rather a thong 704 is provided. The front view 702 of the thong shows similar regions and sections as shown in FIG. 1, but further provides thong anchors 706 and a midline 708. Further, the back portion at 704 is shown a panty liner 710 is shown. The panty liner 710 is similar to the liner of FIG. 1, but it provided as a thong. Side view 712 shows thong back 708.

Figure 8:
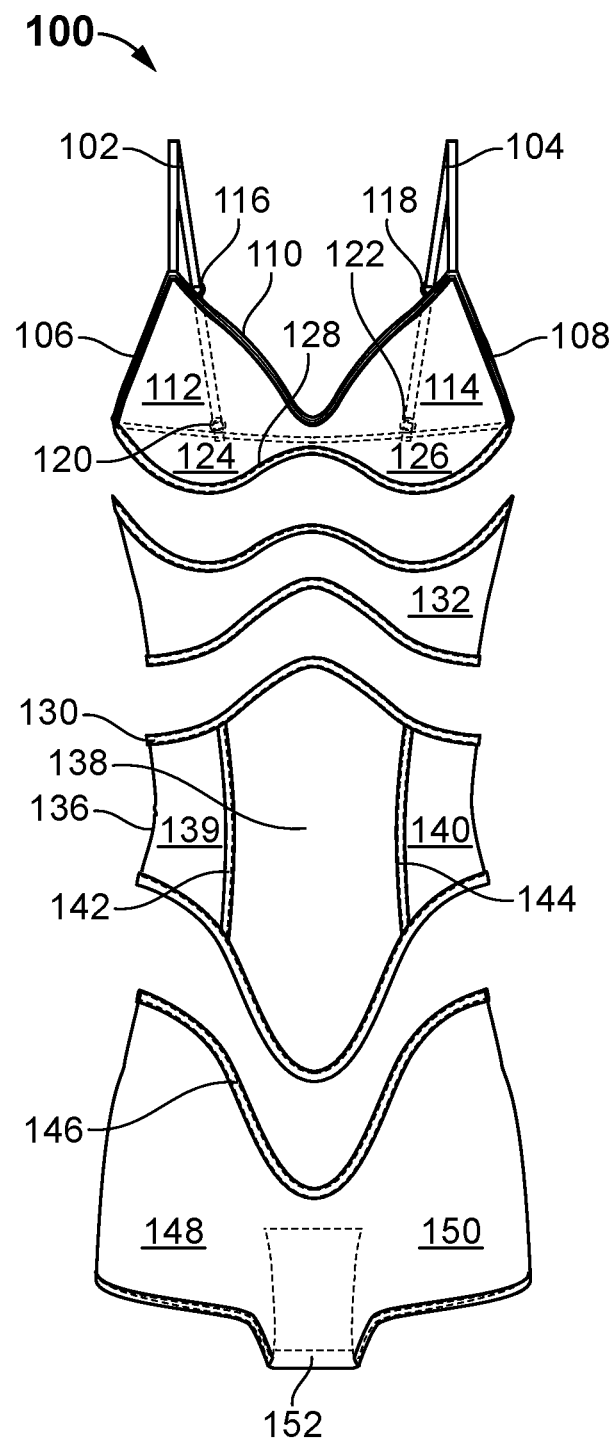
FIG. 8 shows an exploded view of the compression garment according to an embodiment.

Referring now to FIG. 8, an exploded view of FIG. 1 is shown. As in FIG. 1, garment 100 comprises right shoulder strap 102 and left shoulder straps 104, and right adjustable member 116 and a left adjustable member 118 attached to the at least one shoulder strap. A right breast section 112 and a left breast section 114 are provided and are positioned proximate the pectoralis major and deltoid of the user.

The bralette has a top section 10 and right portion 106 and left portion 108 are configured to provide attachment points for the straps 102 and 104. Further, the top section 110 and the first horizontal anchor 128 act to define the breast portions 112 and 114 and under-breast portions 124 and 126.

The latissimus dorsi and serratus anterior section 132 is defined by the first horizontal anchor 128 and second horizontal anchor 130. Below the latissimus dorsi and serratus anterior section 132, an umbilical and hypogastric section 138 is connected thereto. The second horizontal anchor 130 is provided and is positioned at the top of the umbilical and hypogastric section 138. Like the first horizontal anchor 128, the second horizontal anchor 130 is configured to support and define the umbilical and hypogastric section 138, while also providing an anchor point approximately seven (7) millimeters (mm) below a rib line of the user. In operation, the second horizontal anchor 130 has an upward bell curved profile in relation to the user's lower breast 124 and 126. Like the first anchor 128, second anchor may be 130 may be manufactured from a material that has a high tensile strength or may be a seam that protects the stitching thereunder.

Below the umbilical and hypogastric section 138, lumbar and iliac section 148 and 150 is defined by the second anchor 130 and third anchor 146. The third anchor 146 is provided and is positioned at the bottom of the umbilical and hypogastric section 138 and top of the lumbar and iliac section 148 and 150. Like the second horizontal anchor 146, the third horizontal anchor 146 is configured to support and define the umbilical and hypogastric section 138 and the lumbar and iliac section 148 and 150 while also providing an anchor point approximately seven (7) millimeters (mm) below a rib line of the user. The third anchor 146 is positioned approximately seven (7) millimeters (mm) above a hip line of a user, and each anchor portion is configured to compress, smooth, provide separation, structure, support, and shape for smoothing of a user's skin.

Advantageously, the garment of the present disclosure is configured to be worn as a compression garment and undergarment based on its low profile and the materials described herein.

Preferred embodiments of this disclosure are described herein, including the best mode known to the inventors for carrying out the disclosure. It should be understood that the illustrated embodiments are exemplary only and should not be taken as limiting the scope of the disclosure.

The foregoing description comprise illustrative embodiments of the present disclosure. Having thus described exemplary embodiments of the present disclosure, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method. Many modifications and other embodiments of the disclosure will come to mind to one skilled in the art to which this disclosure pertains having the benefit of the teachings in the foregoing descriptions. Although specific terms may be employed herein, they are used only in generic and descriptive sense and not for purposes of limitation. Accordingly, the present disclosure is not limited to the specific embodiments illustrated herein.

What is claimed is:

1. A compression garment for maximizing pressure on a soft-tissue area of a user, the garment comprising:
    a breast section configured for placement proximate a pectoralis major and breast of the user, wherein the breast section is constructed of single layer fabric cut on grain and configured to support the breast section;
    a latissimus dorsi and serratus anterior section connected to the breast section, wherein the latissimus dorsi and serratus anterior section is constructed of the single layer fabric cut on grain;
    a first horizontal anchor positioned at a bottom of the breast section of the garment, wherein the first horizontal anchor is configured to support the latissimus dorsi and serratus anterior section of the user;
    an umbilical and hypogastric section connected to the latissimus dorsi section, wherein the umbilical and hypogastric section is constructed of double-layer fabric cut on cross grain and configured to smooth soft tissue which is configured for placement an umbilical and hypogastric section of the user;
    a second horizontal anchor positioned and connected to a top of the umbilical and hypogastric section, wherein the second horizontal anchor is configured to support an umbilical and hypogastric section of the user;
    a lumbar and iliac section connected to the umbilical and hypogastric section, wherein the lumbar and iliac section is constructed of the single layer fabric cut on grain; and
    a third horizontal anchor positioned and connected to a bottom of the lumbar and iliac section, wherein the third horizontal anchor is configured support a lumbar and iliac section of the user.

2. The compression garment of claim 1, further comprising:
    a left vertical seam connected to the second horizontal anchor and the third horizontal, wherein the first vertical seam defines a left lumbar region of the user;
    a right seam anchor connected to the second horizontal anchor and the third horizontal anchor, wherein the first vertical seam defines a right lumbar region of the user;
    wherein the left vertical seam and right vertical seam are configured to flatten the umbilical and hypogastric section of the user and pull the garment in both a vertical and a horizontal direction to stabilize the garment and the umbilical and hypogastric section of the user.

3. The compression garment of claim 1, wherein:
    the breast section comprises a bralette a V-shaped profile with relation to a user's breast;
    wherein the second horizonal anchor has an upward sinusoidal curved profile in relation to a user's lower breast;
    wherein the second horizontal anchor has an upward bell curve profile in relation to the user's lower breast;
    wherein the fourth horizonal anchor has a downward bell curve profile in relation to the user's lower breast.

4. The compression garment of claim 1, wherein:
    the second anchor is positioned approximately seven (7) millimeters (mm) below a rib line of the user;
    the third anchor is positioned approximately seven (7) millimeters (mm) above a hip line of a user; and
    each of the anchors are configured to compress, smooth, provide separation, structure, support, and shape for smoothing of a user's skin.

5. The compression garment of claim 1, further comprising at least one shoulder strap configured to retain the garment in a vertical position, and further configured to provide lifting support to a breast portion of the user, wherein the shoulder strap is constructed of a double layer suede.

6. The compression garment of claim 5, wherein the at least one shoulder strap comprises at least one adjustable member attached to the at least one shoulder strap, wherein the at least one adjustable member is an O-ring having a rubberized finish and configured to allow a user to adjust the vertical fit of the garment and prevent chafing to the user.

7. The compression garment of claim 1, wherein the breast section, the latissimus dorsi and serratus anterior section, an umbilical and hypogastric section and the lumbar and iliac section is constructed of a mesh.

8. The compression garment of claim 1, further comprising a fastener configured to be positioned on a left or right portion of the user extending from the iliac region to the breast region of the user.

9. The compression garment of claim 8, wherein the fastener is a zipper configured to provides ease of garment entry, exit, and closure, and produce a compression of a user's body when in a closed position.

10. The compression garment of claim 1, further comprising a panty liner cut on grain and attached to the third anchor, wherein the panty liner is double-layered and comprises a snap or self-fabric hook and loop closure.

11. The compression garment of claim 1, wherein the double layer fabric cut on cross-grain is fused with a stretch fabric.

12. The compression garment of claim 11, wherein a first layer of the double layer fabric is a polyester and spandex blend, and the second layer is an applied binding with a luster finish.

13. The compression garment of claim 9, wherein the zipper is a reverse zipper with an internal guard and an exterior reinforcement portion.

14. The compression garment of claim 5, wherein the at least one shoulder strap comprises a pair of shoulder straps, each shoulder of pair of shoulder straps configured to retain the garment in a vertical position, and further configured to provide lifting support to a breast portion of the user, wherein each of the shoulder straps is constructed of a double layer suede.

15. The compression garment of claim 5, wherein the at least one shoulder strap comprises a pair of least one adjustable member attached to the at least one shoulder strap, wherein the at least one adjustable member is an O-ring having a rubberized finish and configured to allow a user to adjust a vertical fit of the garment and prevent chafing to the user.

* * * * *